(12) United States Patent
Kozee et al.

(10) Patent No.: US 9,631,103 B2
(45) Date of Patent: Apr. 25, 2017

(54) COLOR CHANGING INKJET INK COMPOSITION

(71) Applicant: VIDEOJET TECHNOLOGIES INC., Wood Dale, IL (US)

(72) Inventors: Michael Kozee, Wheaton, IL (US); Linfang Zhu, Woodridge, IL (US)

(73) Assignee: Videojet Technologies Inc., Wood Dale, IL (US)

( * ) Notice: Subject to any disclaimer, the term of this patent is extended or adjusted under 35 U.S.C. 154(b) by 13 days.

(21) Appl. No.: 14/405,700

(22) PCT Filed: Jun. 19, 2013

(86) PCT No.: PCT/US2013/046474
§ 371 (c)(1),
(2) Date: Dec. 4, 2014

(87) PCT Pub. No.: WO2013/192268
PCT Pub. Date: Dec. 27, 2013

(65) Prior Publication Data
US 2015/0166806 A1    Jun. 18, 2015

Related U.S. Application Data

(60) Provisional application No. 61/661,658, filed on Jun. 19, 2012.

(51) Int. Cl.
*C09D 11/328* (2014.01)
*C09D 11/36* (2014.01)
*C09D 11/50* (2014.01)
*C08K 5/46* (2006.01)
*C09D 11/52* (2014.01)
*A61F 13/42* (2006.01)

(52) U.S. Cl.
CPC .............. *C09D 11/328* (2013.01); *C08K 5/46* (2013.01); *C09D 11/36* (2013.01); *C09D 11/50* (2013.01); *C09D 11/52* (2013.01); *A61F 2013/422* (2013.01)

(58) Field of Classification Search
CPC ....... A61F 13/42; A61F 13/422; C09D 11/50; C09D 11/328; C09D 11/52; C09D 11/36; C08K 5/46
See application file for complete search history.

(56) References Cited

U.S. PATENT DOCUMENTS

| 5,342,861 A | 8/1994 | Raykovitz |
| 6,904,865 B2 | 6/2005 | Klofta |
| 2003/0154904 A1* | 8/2003 | Klofta ..................... A61F 13/42 116/206 |

(Continued)

FOREIGN PATENT DOCUMENTS

| WO | 2005102238 | 11/2005 |
| WO | 2011103378 | 8/2011 |

*Primary Examiner* — Henok Legesse
(74) *Attorney, Agent, or Firm* — Robert L. Wolter; Beusse, Wolter, Sanks & Maire PLLC (57) ABSTRACT

An ink jet ink composition includes an organic solvent in an amount between 60% and 95% by weight of the ink composition, a binder resin, a stabilizing agent, which may be provided by the binder resin, and a pH sensitive dye. An image formed by the ink composition changes from a first color to a second color when exposed to water, wherein the first color is different than the second color.

20 Claims, 2 Drawing Sheets

(56) References Cited

U.S. PATENT DOCUMENTS

| | | |
|---|---|---|
| 2004/0191118 A1 | 9/2004 | Mody |
| 2006/0149198 A1 | 7/2006 | Liu |
| 2011/0015598 A1 | 1/2011 | Song |
| 2013/0116644 A1* | 5/2013 | Wei .......................... A61L 15/56 |
| | | 604/361 |

* cited by examiner

COLOR CHANGING INKJET INK COMPOSITION

BACKGROUND OF THE INVENTION

The present disclosure relates to color changing inkjet ink compositions and methods of printing on hygienic articles.

Methods have been proposed to indicate wetness in a hygienic article, namely diapers or incontinence pads. For example, the inner surface (or the surface towards the body) of the outer liner of a diaper may have a printed message such as animal figures, alphanumerics, or other patterns attractive to children (infants or toddlers). When the diaper becomes wet and the urine reaches the outer liner, the figure or pattern in the printed message changes. Such changes in the image will be visible to the wearer or caregiver, thereby indicating that a diaper change is required.

To function as an effective wetness indicator, the printed image needs to be suitably attractive to the wearer, provide a first image state and provide a visually distinguishable second image state after incontinence, wherein one or both states should exhibit a high level of contrast. It is often desirable that the second state is darker and even more visible than the first state, so that it is obvious that an action needs to be taken. Since in this case the second state is a positive indication of incontinence, it is preferred that the printed image does not dissolve away, does not revert to the initial state, and remains sharply defined and discernible. The first state also needs to be very stable and not change prior to the incontinence event, even when exposed to, for example, very humid environments.

Currently, wetness indicators that change from lighter to darker image states are provided by hot melt applicators printing glue-like compositions. Due to the relatively large inner bore diameter of the nozzles required to deliver these thick glues, the applied images offer only crude resolutions, no graphics or text are effectively possible, and the indicator glue usages are higher than desired. Another technology used to apply wetness indicators is flexographic contact printing. Flexographic printers, however, cannot deliver images with digital variable information (the ability to change images from one print to the next), require a relatively large footprint on a production line, and thus are not preferred for reasons of inconvenience and cost of integration. For these reasons, flexographically printed hygienic articles are often preprinted in large production batches in secondary processes, which adds cost and complexity to manufacturing.

In contrast, ink jet printing is a well-known technique by which digital printing is accomplished without contact between the printing device and the substrate on which the printed characters are deposited. Inkjet offers the general advantages of high resolution, digital variable information, the ability to deliver relatively controlled doses of fluid, low consumable use, low VOC emissions, and ease of integration. Ink jet printing can be broadly divided into drop-on-demand (DOD) printing and continuous inkjet (CIJ) printing. Binary array, a subset of CIJ inkjet printing, is particularly preferred because it can print at very high production linespeeds in comparison with DOD printing technologies (particularly on a per-printhead basis) and employ solvent based inks exhibiting fast drying rates that enable very fast production speeds on commonly employed web-based production lines while also providing the aforementioned ease of integration.

In general, an ink jet ink composition must meet certain strict requirements to be compatible with ink jet printing systems. These requirements relate to the physical properties of the fluid (such as viscosity), the chemical properties (such as the solubility and compatibility of the components), and the ability to suitably wet the substrate. Further, the ink must be quick drying and smear resistant, and be capable of passing through the ink jet nozzle(s) without clogging, and permit rapid cleanup of the machine components with minimum effort. The selection of fast drying, durable polymers for inkjet inks requires both strong theoretical understanding of these properties as well as empirical validation of their performance. Binary array printing furthermore requires the use of polymers with a highly specific set of molecular properties. Also, binary array like CIJ generally employs an electrostatic mechanism to control drop placement and thus requires an ink composition that is sufficiently conductive and chargeable. At present, there are no color changing inkjet compositions that provide the performance as described above as well as compatibility with desired printers. In fact, it is highly difficult to formulate an inkjet ink with low viscosity, low solids and high volatility that also provides images with good ambient color stability and rapid color change.

Current ink jet formulations that function as wetness indicators rely on a mechanism that washes the ink away from the surface of the printed article. These inks include water-soluble ingredients and as they wash away after contact with bodily fluids the images will change from a darker to a lighter perceived color. In such current wetness indicators the final image is not usually completely removed even after a long period of aqueous exposure, resulting in a muddled and unattractive appearance as opposed to being easy to interpret by the wearer or caregiver.

Hence, there is generally a need for inkjet formulations and methods that enable the online application of effective color changing wetness indicators with more attractive patterns, more positive and safe indicating end-points, reduced materials use, and that are able to be easily integrated, as compared with the prior art methods.

BRIEF SUMMARY OF THE INVENTION

The disclosure provides methods of printing an image to serve as a wetness indicator on hygienic articles.

In one aspect, an ink jet ink composition includes an organic solvent in an amount between 60% and 95% by weight of the ink composition, a binder resin, a stabilizing agent, which may be provided by the binder resin, and a pH sensitive dye. An image formed by the ink composition changes from a first color to a second color when exposed to water, wherein the first color is different than the second color.

In another aspect, a method of printing on a hygienic article includes applying droplets of an ink composition with an ink jet printer in a single pass to a surface of a hygienic article to form a desired image. The ink composition includes an organic solvent in amount between 60% and 95% by weight of the ink composition, a binder resin, a stabilizing agent, which may be provided by the binder resin, and a pH sensitive dye. The image acts as a wetness indicator by changing from a first color to a second color when exposed to an aqueous solution, wherein the first color is different than the second color.

DETAILED DESCRIPTION OF THE INVENTION

The disclosure relates to a color changing ink composition and methods of printing on hygienic articles, such as baby diapers, adult incontinence pads, or feminine pads. The ink compositions can be printed using an inkjet printer to produce images that change from an initial color to a different final color. The printed images are intended to be a wetness indicator for disposable diapers by interacting with urine or other bodily fluids after a specified time to develop an initial to end-point color change that is visually perceptible. The most preferred embodiment is one where the color changes from light to dark. The wetness indicator image changes when exposed to aqueous bodily fluids to provide an indication that the diaper or other hygienic article has been soiled. This indicator thus provides a visual cue to the wearer or the caregiver that the article needs to be changed. The printing method preferably uses digital ink jet printing systems, particularly binary array ink jet printers. The printed image which yields the desired color change can be delivered in a single-pass printing step.

The inks of the present invention are applied using ink jet printing without direct contact between the printing device and the substrate on which the printed characters are deposited. Briefly described, ink jet printing involves projecting a stream of ink droplets to a surface in a controlled manner so that the droplets are caused to form the desired printed image on that surface. This technique of noncontact printing is particularly well suited for the application of characters onto substrates such as diapers. Ink jet printing can be broadly divided into drop-on-demand (DOD) printing and continuous inkjet (CIJ) printing. For the majority of DOD printers, droplets are produced as needed from a resting fluid state by one of two technical premises to form an image on the substrate—either by the movement of a piezoelectric element or by the thermal generation of a bubble by a technology termed thermal ink jet (TIJ). In CIJ printing in contrast, the ink continuously flows through the nozzle(s) and droplets are also produced continuously, and only a fraction of the droplets are used to form an image. During CIJ printing, the droplets are typically directed away from the continuous stream by selectively charging each droplet and deflecting or attracting the charged ones using an electric field or a charged surface. For example, printed droplets may be charged and deflected to form the print image and the non-charged drops may be returned to the gutter. The relative amount of charge placed on each droplet determines the relative position of the resulting printed drops on the substrate. For binary array technology which is a specific subset of CIJ technology, the non-printed droplets are typically charged and deflected to the gutter and the printed droplets are not charged. As is the case with DOD technology, the relative positions of the nozzles in the array determine the relative position of the printed droplets. There are other means and mechanisms by which drops may be selected and printed in CIJ printers and the above description is not intended to be limiting.

There are several advantages with the latter mentioned binary array technology over other inkjet printing technologies. In comparison to the single nozzle CIJ technology, binary array offers better print quality because the alignment of the printed droplets does not depend on the ability to accurately charge these droplets while in-flight. In addition, due to the high number of nozzle orifices in a potential nozzle array, binary array is particularly advantaged to print large graphics or multiple lined text images, for example, at high line speeds.

For the production of hygienic articles, inks are preferably laid down within a single pass of the printhead over the same area of the substrate and printers should be easily incorporated into existing production lines. Digital printers based on DOD piezo or TIJ technology cannot typically apply enough ink volume during a single pass at very high production line speeds to achieve a high degree of print color contrast. To render an image, CIJ or binary array ink contrast may generate 60,000 or even 100,000 or more droplets in a second per nozzle. As compared with drop-on-demand ink jet, a relatively higher volume of ink can be delivered per droplet and/or per printhead. If needed, printed spot sizes may be modulated by applying multiple printed droplets at essentially the same physical spot to promote the printed color and contrast. In addition, piezo DOD inks are typically based on oil or other non-volatile solvents and thus do not dry on non-porous or semi-porous substrates. TIJ inks are typically water based and contain a substantial amount of non-volatile solvents which is, again, not suited for printing on non-porous and semi-porous plastic films or non-woven materials. Conventional contact printing methods such as flexography require a relatively large footprint on a production line and thus are not preferred typically for reasons of inconvenience and cost of integration.

An image formed by the ink composition changes from a first color to a second color when exposed to water or other aqueous solution, wherein the first color is different than the second color. The printed images-either before or after interaction with aqueous fluids—should have sufficient visibility or contrast and a desired color when printed on non-porous or semi-porous materials, such as plastic films. The image may be any suitable color as defined by the Pantone® color space or other equivalent methods. The wetness indicator image should change color rapidly enough when exposed to water or bodily fluids to provide a timely indication that the diaper or other hygienic article is soiled. After coming directly in contact with aqueous fluids such as urine, the image changes color within a short period of time (e.g., less than 10 minutes, preferably less than 2 minutes, most preferably less than 30 seconds). The color change is easily perceptible to the naked eye exhibiting a $\Delta E$ (as determined by CIELAB $L^*a^*b^*$ measures) greater than 5 and more preferably $\Delta E$ greater than 10. The image furthermore does not dissolve away and remains sharp and well-defined during the color change event and well afterwards.

The initial image should also be sufficiently stable so as to not be easily degraded (e.g., to remain color-stable) even when exposed to high ambient humidity levels for long periods of time as would be expected during storage or use of the articles prior to insult. For example, when printed images are stored at ambient conditions of 40° C. and 85% relative humidity, the images preferably do not appreciably change color (e.g. a $\Delta E$ of less than 4).

The ink composition includes an organic solvent, a binder resin, a stabilizing agent (which may be provided by the binder resin), and a pH sensitive dye. The ink composition may also include a conductive salt that is compatible with the color changing mechanism. The ink composition may include one or more stabilizing agents with acid numbers of at least 100 that are generally water insoluble or immiscible.

In one embodiment, the ink composition includes one or more pH sensitive dyes which react with acids or bases to change color. The dyes can be selected from those that when exposed to an aqueous environments change color within a pH range of about 0 to about 15 or more preferably within a pH range between 3 and 9.

Examples of suitable dyes may be chosen from the class of brominated phenolsulfonphthaleins. Examples of these dyes include but are not limited to bromophenol blue, bromocresol green, bromocresol purple, bromothymol blue, and the like. Other dyes or dye classes pertinent to the invention are m-cresol purple, cresol red, chlorophenol red, acridine, acridine orange base, m-cresol purple, tetrabromophenolphthaleine ethyl ester, and tetrabromobenzalaniline. The dye can be present in an amount from 0.1% to 10%, preferably from 0.2% to 5%, and more preferably from 0.3% to 1% by weight of the ink composition.

The use of pH sensitive dyes to provide for a different initial and final color after aqueous exposure does not preclude the use of additional pH insensitive dyes that do not participate in the color change but are intended to lend to a specific desired color.

The ink compositions contain one or more carrier solvents with a weight percent range of about 50% to about 99%, and preferably about 60% to 95%, and more preferably 70% to 90% by weight of the ink composition. The total amount of the organic solvents can be in any suitable amount, for example, in an amount 60% or more, 70% or more, or 80% or more by weight of the ink composition. Preferably, the carrier solvents are organic solvents. More preferably, the organic solvents are volatile organic solvents with relative evaporation rates greater than about 0.1 relative to n-butyl acetate, and even more preferably greater than 1.0. The organic solvents are selected from ketones, lower order alcohols (i.e., ethanol, isopropanol, n-propanol, t-butanol, iso-butanol, n-butanol), carbonates (i.e., dimethyl carbonate), glycol ethers, esters, glycol ether acetates, and mixtures thereof. The organic solvents are preferably selected from $C_1$-$C_4$ alcohols, $C_3$-$C_6$ ketones, and mixtures thereof. Examples of $C_3$-$C_6$ ketones include acetone, methyl ethyl ketone, methyl n-propyl ketone, and cyclohexanone. Examples of $C_1$-$C_4$ alcohols include methanol, ethanol, 1-propanol, n-butanol and 2-propanol. The organic solvents, particularly alcohols and ketones, enable the sufficient wetting and penetration of semi- and non-porous substrate surfaces and, as mentioned before, rapid drying ink drying time. It is believed, without being bound to theory, that due to ink penetration, the visually perceptible contrast on the outwardly facing non-printed surface of the outer liner is improved over hot-melt indicators.

In particular embodiments, the ink composition includes, as the organic solvent(s), acetone or a blends of acetone and lower order alcohols such as ethanol. The most preferred solvents are acetone, ethanol, and mixtures thereof. In an embodiment, the organic solvents used include acetone and ethanol. The acetone may be present in an amount between 40% and 99% by weight, preferably between 50% to 80% by weight of the ink composition. The ethanol may be present in an amount between 0.1% and 60% by weight, preferably between 5% and 35% by weight of the ink composition.

The ink composition may include a binder resin for adhering to non-porous substrates and to protect the printed image from dissolution by aqueous solutions and ambient moisture. More than one resin can be used. The binder resin can be present in any suitable amount, for example, in an amount from 0.1% to 30%, preferably from 0.5% to 25%, and more preferably from 2% to 15% of the ink composition. Any suitable resin may be used. Preferably the resin is completely soluble in the ink composition but substantially insoluble in water. Examples of suitable polymer classes are acrylic, styrene-acrylic, vinyl, vinylbutyral, vinyl pyrrolidone, polyamide, polyurethane, phenolic, polyketone, formaldehyde, alkyd, alkyd esters, modified cellulose (i.e., hydroxypropylcellulose), cellulose ester, cellulose ether, and nitrocellulose. Preferred specific examples include cellulose esters such as cellulose acetate butyrate and cellulose acetate propionate. Particularly suitable fixative resins are ones that have molecular weights (Mw) between about 20,000 and 120,000 Daltons and glass transition temperatures ($T_g$) between 70 and 180° C. The compositions can be formulated to be compatible with impulse DOD (including piezo and TIJ) or continuous inkjet printing (CIJ) technologies. Typical DOD ink jet inks have viscosities between about 3 and 35 cP at 25° C. Typical CIJ inks have viscosities of about 1.5 to 7 cP.

Ink compositions for the continuous inkjet process should exhibit solution conductivities greater than 200 microSiemens, and more preferably greater than 500 microSiemens. Conductive agents may be defined as an ionic species added to the ink composition to impart measurable conductivity. Preferred conductive agents are cation/anion pairs where the salts are selected based on cations of alkali earth metals, alkali metals (i.e., $Li^+$, $Na^+$, $K^+$), ammonium, alkyl/aryl ammonium and alkyl/aryl phosphonium, and the like. Typical anions for the cation/anion pairs are halides, halophosphates (e.g., hexafluorophosphate), halo-antimonates, halo-borates, phenyl borates, nitrates, phosphates, sulfates, phosphonates, sulfonates, carbonates, carboxylates, thiocyanates, acetates, triflates, tosylates and the like. Conductive agents are typically only added to impart just enough electrical conductivity. In a typical ink composition, conductive agents are provided in an amount from 0.1 to 2.5% by weight of the ink composition.

The ink composition may also include one or more stabilizing agents in amount from 1% to 30% by weight of the ink composition. The stabilizing agents may be intentionally added acidic or basic species that are soluble in the ink in order to lend stability to the pH sensitive dye—i.e., so that it does not prematurely change color in solution or in the dried state. Acid stabilizing agents have been found to provide the printed image added resistance to high ambient humidity particularly when printed on semi-porous films. Suitable classes of stabilizing acids may include inorganic or organic acids. For example, inorganic acids can be conjugate acid analogues of the following conjugate base anions: phosphates, phosphonates, sulfates, halides, carbonates, borates, sulfonates, thiocyanates, citrate, etc. Suitable examples of organic acids would be any molecule containing an organic (C—H) moiety covalently bound to a conjugate acid analogue of any of the following conjugate bases: acetates, sulfonates, phosphonates, citrates, etc. Organic acids may be monomeric or polymeric and can further include alkyl aliphatic and/or aromatic acids. More specifically, suitable organic acid polymers include organic acidic polymers containing carboxyl or anhydride functional groups such as styrene-acrylic acid, acrylate-acrylic acid (i.e., methacrylate-acrylic acid or methacrylic acid), acidic rosin esters, styrene-maleic anhydride copolymers, and acidic sulfonated polymers such as sulfonated polyesters, phosphoesters, etc. Preferably organic acids will exhibit an acid number between about 100 to about 1000 and, more preferably, acid numbers between 150 and 500. Basic stabilizing agents may be any inorganic or organic base including the conjugate bases for the acids listed above.

Without being bound to theory, it is believed that good image color stability is afforded by acids with a high relative number of pH-active groups per molecule that can change the local pH environment of the dye after drying. It is also believed that the best stabilizing agents are those that after drying are largely water insoluble or immiscible and thus also prevent ingress of gaseous water. Specific water insoluble examples include resins incorporating acrylic acid groups as well as styrenated monomers which improve water resistance. The most preferable acidic polymers have a minimum average molecular weight (Mw) of 500. Other specific non-polymeric examples include fatty acids such as lauric acid, decanoic acid, oleic acid, and myristic acid.

The composition may also include one or more additives that serve as color changing promoters that increase the rate of color change. Such components are largely water soluble or water miscible and comprise solids or liquids. For this purpose, water soluble inorganic salts may be used in excess in the solvent-based formulation over that which is required to achieve nominal solution conductivity. Without intending to limit the scope of which salts could be effective, specific examples of salts that are both water soluble and solvent soluble are lithium salts such as lithium triflate (FC-122) or lithium nitrate; salts containing tetraalkyl/aryl ammonium cations (i.e., tetrabutylammonium bromide, tetrabutylammonium nitrate, etc.), and, thiocyanate salts such as potassium thiocyanate. For example, FC-122 is typically only required at around 0.5 weight percentage in an acetone/ethanol solvent based CIJ ink. To function as an effective color changing promoter, the ink composition may include FC-122 in an amount greater than 1% and more preferably greater than 2% by weight of the ink composition.

Examples of suitable liquid color changing promoters include non-volatile, highly water miscible organic solvents such as glycols (such as propylene glycol), diols such as hexanediol, triols such as glycerol, or polyols such as polyethylene glycol, polypropylene glycol and the like. Color changing promoters may be present in the formulation in any amount ranging between 0 to 10% by weight of the composition.

The ink composition can further include one or more additives such as surfactants and/or plasticizers, for example, to improve dot definition on a particular substrate. Any suitable surfactant can be used, for example, a surfactant selected from the group consisting of anionic surfactants, cationic surfactants, non-ionic surfactants, polymeric surfactants. Examples of surfactants include modified polysiloxanes, alkyl modified polyoxyalkyleneamines, alkyl modified propoxylated (poly(oxypropylene)) diamines, alkyl ether amines, nonyl phenol ethoxylates, ethoxylated fatty amines, fluorinated organic acid diethanolamine salts, alkoxylated ethylenediamines, alkyl modified polyethylene oxides, alkyl modified polyalkyleneoxides, alkyl phosphate ethoxylate mixtures, polyoxyalkylene derivatives of propylene glycol, polyoxyethylated fatty alcohols, and salt of fatty acids. In any of the embodiments, the surfactants can be present in an amount from about 0.001 to about 2.0%, preferably from about 0.02 to about 1%, and more preferably from about 0.03 to about 0.5% of the ink composition.

Examples of suitable plasticizers include phthalate plasticizers, e.g., alkyl benzyl phthalates, butyl benzyl phthalate, dioctyl phthalate, diisobutyl phthalate, dicyclohexyl phthalate, diethyl phthalate, dimethyl isophthalate, dibutyl phthalate, and dimethyl phthalate, esters such as di-(2-ethylhexy)-adipate, diisobutyl adipate, glycerol tribenzoate, sucrose benzoate, dibutyl sebacate, dibutyl maleate, polypropylene glycol dibenzoate, neopentyl glycol dibenzoate, dibutyl sebacate, and tri-n-hexyltrimellitate, phosphates such as tricresyl phosphate, dibutyl phosphate, triethyl citrate, tributyl citrate, acetyl tri-n-butyl citrate, polyurethanes, polyacrylics, lactates and sulfonamide plasticizers such as Plasticizer 8, available from Monsanto Co., St. Louis, Mo., which is n-ethyl o,p-toluene sulfonamide. In certain embodiments, the plasticizer can be present in an amount from about 0.1 to about 5.0%, preferably from about 0.2 to about 3.0%, and more preferably from about 0.25 to about 2.0% of the ink composition.

The ink composition can have any suitable viscosity or surface tension. The ink composition while jetting preferably has a viscosity at 25° C. between 1 and 10 cPs, preferably between 1.5 and 7.0 cPs, and most preferably between 2.5 and 5.0 cPs. The ink composition preferably has a surface tension defined by the bubble-tensiometer method from about 20 to about 50 $mNm^{-1}$, from about 21 to about 40 $mN\ m^{-1}$, or from about 22 to about 30 $mN\ m^{-1}$ at 25° C. The solids (at 25° C.) content of the ink composition may be equal to or less than 100% by weight, more preferably less than 40% and is most preferably less than 30% by weight. The resulting sonic velocity of the ink is preferably between 1100 and 1600 meters per second as measured by the acoustic method.

The ink composition can be prepared by any suitable method. For example, the chosen ingredients can be combined and mixed with adequate stirring and the resulting fluid filtered to remove any undissolved impurities.

In one embodiment, the ink composition used herein is not a hot melt ink composition, which is defined as an ink that is jettable at higher temperature but that exhibits a solids content at 25° C. that is greater than 90%. Existing diaper light to dark color changing wetness indicators are mostly hot melt glue based compositions. Similar indicators are also used for adult incontinence products, as these provide highly visible color indication and are located through the crotch region where they are visible to a caregiver while the wearer is lying down. Hot melt stripes are generally applied from two or three large bore glue nozzles that lay down relatively simple stripes or dots due to the resolution limitations of the glue applicator. These low resolution patterns are far less desirable from a product marketing perspective than higher resolution images created by inkjet. In typical hot melt systems, a large amount of glue is applied to each printed article (generally >20 mg), yielding higher materials cost per printed article as compared with the current method which delivers equivalent or better performance employing one tenth or less of the amount of printed material. In another embodiment, the ink compositions disclosed herein may be formulated as part of a hot melt composition.

As described above, a preferred embodiment is for the images to be applied digitally with a binary array printer that prints at high production speeds and is easy to integrate into production lines. Since one fluid delivers dyes that are responsible for both initial and final color, only a single print head or nozzle bank is required to deliver the printed image in a single pass. The images may be jet printed directly onto the substrate during either the assembly or packaging stages of a web-based disposable diaper production process, allowing flexibility to change images in the middle of a production run and without the need to maintain inventories of different preprinted substrates.

The printing system used to apply the ink composition to provide the printed image is preferably a binary array printing system, preferably a BX printer available from Videojet Technologies Inc. A suitable specific example is the Videojet® BX6000 series (single head and dual headed versions). The BX printing system delivers a number of reliability advantages in industrial applications by virtue of its design. For printing on hygienic articles, it is desirable to be able to print an image at least 2 inches wide with a resolution of at least a 100 dpi (horizontal and vertical). High speed digital printing methods are generally limited to a width of a few inches. The printer is preferably capable of printing with the desired print quality while the substrate is moving at a high speed. For example, the hygienic article may move with respect to the inkjet printer at a speed of greater than 1000 ft/min, or greater than 1500 ft/min, or greater than 1750 feet/min, or greater than 2000 ft/min during printing. Binary array printers are capable of meeting these application specifications.

As previously described, the hygienic articles include an image that acts as a wetness indicator. The image preferably changes from a one image color to a different image color to indicate that the article is wet. In one embodiment, the image changes from a lighter image color to a darker, more visible, image color to indicate the article is wet. The printing method may be used for any type of hygienic article. The hygienic article (such as a diaper) may include a plurality of component materials. For example, a diaper may include a backsheet, a topsheet, an acquisition layer, and an absorbent core disposed between a body contacting surface and a garment contacting surface. The outermost surface of the backsheet may form the garment contacting surface, while the innermost surface of the topsheet may form the body contacting surface. The backsheet typically serves to both encase the absorbent components and provide the printing substrate for the user-visible graphics. It is also termed the 'outer liner' for sake of clarity herein.

The wetness indicator image can be located on or against any surface of a component material, including the body contacting surface and the garment contacting surface, provided that the wetness indicator remains visible from the exterior of the absorbent article. Examples of the location include the backsheet, the topsheet, the acquisition layer, and the absorbent core. The preferred printing surface is the inside surface of the backsheet The ink compositions of can effectively function across a range of materials used in these article constructs. The base material onto which the droplets are deposited is typically a plastic film or a non-woven material or a composite layer which may be multiple films or composites structures containing both woven or non-woven porous materials and films. The porous materials may include fibrous networks or melt-blown type loose networks. The material used to construct the films or layers may be derived from either naturally occurring or synthetic fibers or combinations thereof.

Substrates of particular interest are semi-porous plastic films that are commonly used to enhance the properties (i.e., pliability, resilience or breathability) of the overall diaper construct. When viewed under high magnification, the surfaces of such material tend to exhibit a microporous network with inter-pore spacings on the order of less than 100 microns. When printed on these kinds of films, the disclosed ink composition adheres well and can function after penetrating into the microporous network. The construction materials are most typically polyethylene or polypropylene, but may be made of any suitable plastic material. The inks generally provide good print quality on substrates with surface energies between 18 and 50 mN m$^{-1}$.

The substrates may further be translucent without pigmentation or semi-opaque to opaque comprising pigment fillers. The fillers used (such as calcium carbonate or barium sulfate) tend to be pH active and may impact the performance of any wetness indicators that use pH sensitive colorants particularly because the pH of the aqueous insult solution may change as it passes through such fillers. In an optional embodiment, the basic receptivity of the dried ink compositions here is tailored for a specific substrate. The basicity or alkalinity can be characterized, for example, by exposing a known quantity of the substrate to distilled water under a specific set of conditions and analyzing the resulting pH of the water extract. Knowing the pH of the aqueous extract, inks of this embodiment can be tuned to provide printed images that work with substrates of different alkalinities.

EXAMPLES

Example 1

A buffer solution (Buffer A) including $K_x(NH_4)_y H_{(3-x-y)} PO_4$ was used to mimic urine exposure. The solution was created by adding 5 grams $K_3PO_4$ in 2000 mL of deionized water and titrating the solution to pH=5.0 with 85% $H_3PO_4$. The final buffer pH was controlled by back titrating the acidified solution to pH=6.2 with concentrated ammonia.

An ink composition was prepared using the components listed in Table 1 below. The formulation was prepared and filtered using ordinary methods used for inkjet printing. All properties were measured at a solution temperature of 25° C. The ink composition possessed suitable viscosity, velocity of sound, and solution resistivity for CIJ printing.

TABLE 1

| Material | Weight % |
| --- | --- |
| acetone | 66 |
| deionized water | 1.0 |
| CAB 551-0.01 | 8.0 |
| Joncryl 682 | 10.5 |
| denatured ethanol | 10.0 |
| oleic acid | 3.5 |
| FC-122 | 0.6 |
| bromophenol blue | 0.4 |
| Total % | 100.0 |

Material descriptions: FC-122 is lithium triflate from 3-M Corporation. Bromophenol blue (BPB) is a pH indicating dye in the free acid form and was obtained from Aldrich Corporation. Acetone was obtained from Ashland Chemical, Inc. Denatured ethanol was an ethanol (also obtained from Ashland) containing >90.1% ethanol and <10% organic denaturants. CAB 551-0.01 binder resin is a version of cellulose acetate butyrate (cellulose ester) obtained from Eastman Chemical, Inc with a Mw of about 35,000 and a $T_g$ of 85° C. Joncryl 682 a first pH modifier was obtained from BASF, Inc. Oleic acid, a second pH modifier, was obtained as the FCC grade from Aldrich, Inc.

Graphical images of Example 1 were printed using a Videojet® single nozzle CIJ inkjet printer. After printing, images were tested directly against two comparative examples, both of which were store-purchased diapers. Comparative Example A was a baby diaper with a yellow hot melt applied indicator stripe. Comparative Example B was an adult incontinence diaper with a similarly applied yellow hot melt indicator stripe. To test color change response and magnitude under like-to-like conditions, the printed films were tested apart from the diaper construct—i.e., the backsheet films including any existing indicator stripes were permanently cut-away from the diaper constructs prior to testing. Example 1 was printed onto the same plastic film as comparative Example B. The results from these tests are set forth in Table 2 below. The samples were exposed to Buffer A for ten minutes and the final resulting colors observed and measured.

TABLE 2

| Product/ink | Comparative Example A | Comparative Example B | Example 1 |
|---|---|---|---|
| Initial color | Light yellow | Light yellow | Light yellow |
| Color change after 10 minutes direct Buffer A exposure | Green | Green | Green |
| Δ E after 10 minutes direct Buffer A exposure | 9.8 | 14.5 | 14.6 |
| Color change after 18 days at 40° C./85% R.H. (full article) | Slightly darker yellow | Slightly darker yellow | Slightly darker yellow |
| Δ E after 18 days at 40° C./85% R.H. | 3.1 | 2.6 | 3.3 |

Figure 1:
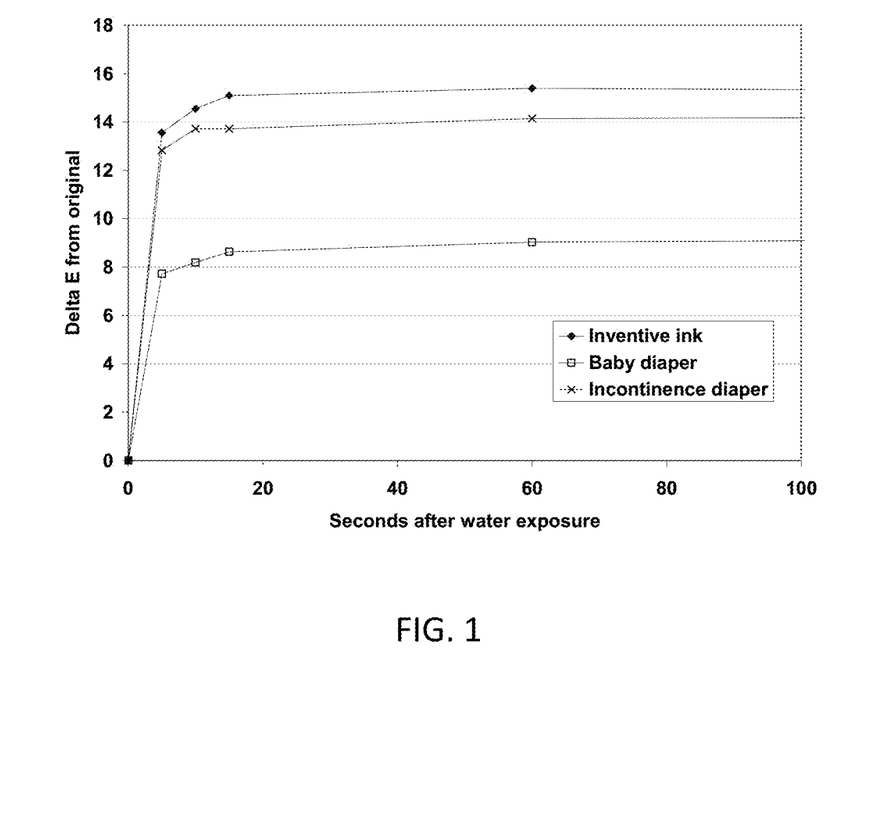
FIG. 1 is a graph showing the color response as a function of time for certain Examples.

The initial and final colors after exposing the printed marks with Buffer A were similar for all three Examples. For Example 1, the color change (ΔE=14.6) was measured to be as good or better than the Comparative Examples. The comparative color responses as a function of time for the first sixty seconds of exposure for the three Examples are further provided graphically in FIG. 1. As can be seen in FIG. 1, under conditions of direct aqueous exposure Example 1 changes color at least as rapidly as the Comparative Examples. Also shown in Table 2, a humidity stability test was performed over a period of 18 days under very humid conditions (40° C. and 85% relative humidity). To do this a sample diaper from which the film was originally cut-away for printing was re-assembled (by taping) with the image facing toward the inside of the diaper construct. The resulting complete, functioning diaper was compared with the store purchased Comparative Examples. Under these conditions, there was little or no color change for any of the examples (each exhibited a ΔE<4).

Figure 2:
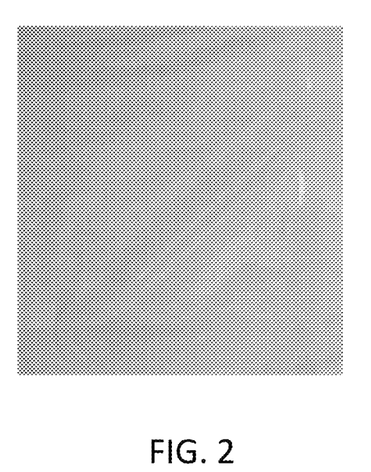
FIG. 2 is a photo showing a printed image prior to exposure to water.
Figure 3:
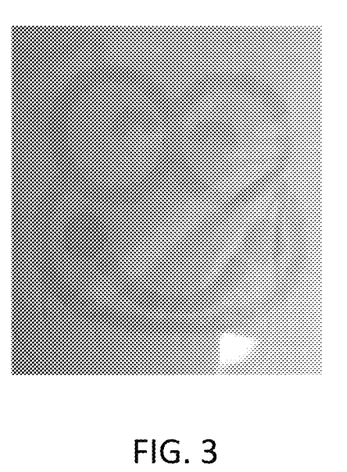
FIG. 3 is a photo showing a printed image after exposure to water.

The ink composition from Example 1 was further tested by printing in a Videojet® BX 6600 series array printer at 128×128 dpi. Several different digital images were printed onto a piece of polyolefin backsheet films that were isolated from three different store bought diapers. The drying time of the printed image was less than 3 seconds. Printed graphic backsheets were then, as described above, re-assembled to yield fully functional diapers each with the printed image on the inner surface facing the absorbent core and the reverse image showing through the backsheet (or outer liner). Enough Buffer A solution was then applied to the inside of the absorbent core so as to simulate an insult event. The images turned color from a barely-visible light yellow to a highly-visible green within about 30 minutes as is depicted in FIGS. 2 and 3. Both the exposed (green) and non-exposed (green) portions of the printed images were also stable with respect to color change at ambient humidities for several months.

Examples 2-6

It was also determined that buffer suitable color response could be achieved by acidic stabilizing agents and/or using additional specific water soluble color promoting additives. The results from printing and testing these combinations are provided in Table 3 below.

TABLE 3

| | Weight % | | | | |
|---|---|---|---|---|---|
| Component | Comparative Example C | Example 2 | Example 3 | Example 4 | Example 5 |
| acetone | 47.5 | 37.2 | 41.7 | 42 | 46 |
| denatured ethanol | 43.1 | 33.8 | 38.0 | 38.2 | 35.9 |
| CAB 551-0.01 | 8.4 | 9.0 | 7.7 | 7.7 | 10.0 |
| Joncryl 682 | | 12.0 | 5.9 | 5.9 | |
| oleic Acid | | 7.0 | | | 7.1 |
| 1,6-hexanediol | | | 5.7 | | |
| FC-122 | 0.5 | 0.5 | 0.5 | 5.7 | 0.5 |
| bromophenol blue | 0.5 | 0.5 | 0.5 | 0.5 | |
| bromocresol green | | | | | 0.5 |
| Total | 100.0 | 100.0 | 100.0 | 100.0 | 100.0 |
| Color after high humidity test | Blue | Yellow | Greenish yellow | Greenish yellow | Yellow |
| Color after exposure to Buffer A, 30 minutes | Green | Blue | Green | Blue-green | Light green |

Material descriptions: Bromocresol green is a pH indicating dye in the free acid form and was obtained from Aldrich Corporation. 1,6-hexanediol was also obtained from Aldrich Corporation.

All properties were measured at a solution temperature of 25° C. The ink compositions possessed suitable viscosities, velocity of sounds, and solution conductivities for continuous inkjet printing. Similar to Example 1, samples of each ink were printed onto diaper films using a CIJ printer and the images were tested with respect to humidity resistance and color responsiveness after direct exposure to Buffer A for up to 30 minutes. As shown in Table 2, Examples 2 to Example 5, which each contained acid stabilizing agents, were more humidity-stable than Comparative Example C, which did not include a stabilizing agent. Also, each of Examples 2-5 exhibited a final color that was visibly distinguishable from the initial color. Example 3-4 which contained higher amounts of water soluble components (1,6-hexanediol or additional salt, FC-122) exhibited strong color endpoints as compared with Comparative Example C while still exhibiting good humidity resistance.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An ink jet ink composition to be applied by an ink jet printer, the ink jet composition comprising:
   an organic solvent in an amount between 60% and 95% by weight of the ink composition;
   a binder resin;
   at least one stabilizing agent, which optionally is provided by the binder resin;
   a pH sensitive dye, wherein an image formed by the ink composition changes from a first color to a second color when exposed to an aqueous solution, wherein the first color is different from the second color; and
   a conductive agent of salts such that the ink jet composition has a conductivity greater than 200 microSiemens.

2. The ink jet composition to be applied by an ink jet printer of claim 1 wherein the at least one stabilizing agent comprises an acid that is water insoluble or immiscible.

3. The ink jet composition to be applied by an ink jet printer of claim 1 wherein the at least one stabilizing agent comprises an acidic polymer.

4. The ink jet composition to be applied by an ink jet printer of claim 1 wherein the change from the first color to the second color occurs in less than 10 minutes and a delta E, as determined by CIELAB L*a*b* measures, between the first and second color is greater than 10.

5. The ink jet composition to be applied by an ink jet printer of claim 1 wherein the at least one stabilizing agent comprises an organic acid with an acid number of at least 100.

6. The ink jet composition to be applied by an ink jet printer of claim 1 wherein the at least one stabilizing agent comprises a fatty acid.

7. The ink jet composition to be applied by an ink jet printer of claim 6 wherein the fatty acid is selected from oleic acid, myristic acid, benzoic acid, and mixtures thereof.

8. The ink jet composition to be applied by an ink jet printer of claim 1 wherein the pH sensitive dye is a brominated phenolsulfonphthalein.

9. The ink jet composition to be applied by an ink jet printer of claim 8 wherein the brominated phenolsulfonphthalein is selected from bromphenol blue, bromocresol green, bromocresol purple, bromothymol blue, and mixtures thereof.

10. The ink jet composition to be applied by an ink jet printer of claim 1 wherein the solvent is selected from ketones, alcohols, and mixtures thereof.

11. The ink jet composition to be applied by an ink jet printer of claim 10 wherein the solvent is selected from ethanol, acetone, and mixtures thereof.

12. The ink jet composition to be applied by an ink jet printer of claim 1 wherein the binder resin is substantially insoluble in water.

13. The ink jet composition to be applied by an ink jet printer of claim 1 wherein the binder resin is a derivative of cellulose including the classes of cellulose esters and cellulose nitrates.

14. The ink jet composition to be applied by an ink jet printer of claim 1 wherein the binder resin has a weight average molecular weight (Mw) between about 20,000 and 120,000 Daltons and a $T_g$ (glass transition temperature) between 70 and 180° C.

15. The ink jet composition to be applied by an ink jet printer of claim 1 further comprising a color changing promoter.

16. The ink jet composition to be applied by an ink jet printer of claim 15 wherein the color changing promoter is selected from a salt exhibiting both good solvent and water solubility or a non-volatile water soluble or miscible solvent.

17. The ink jet composition to be applied by an ink jet printer of claim 15 wherein the color changing promoter comprises a diol, triol, glycol or polyol.

18. The ink jet composition to be applied by an ink jet printer of claim 1 wherein the conductive agent of salts comprises cations selected from lithium, sodium, potassium, and mixtures thereof, and anions selected from nitrate, triflate, iodide, bromide, acetate and mixtures thereof.

19. The ink jet composition to be applied by an ink jet printer of claim 1 wherein the aqueous solution is urine.

20. The ink jet composition to be applied by an ink jet printer of claim 1, wherein the conductivity of the composition is greater than 500 microSiemens.

* * * * *